United States Patent [19]

Leveque et al.

[11] 4,297,884

[45] Nov. 3, 1981

[54] METHOD OF AND APPARATUS FOR THE MEASUREMENT OF AT LEAST ONE MECHANICAL PROPERTY OF AN ELASTIC MATERIAL

[75] Inventors: Jean-Luc Lêvêque, Montfermeil; Laurent Rasseneur, Thorigny-sur-Marne; Jean P. de Rigal, Claye Souilly; Gilbert Gras, Aulnay Sous Bois, all of France

[73] Assignee: L'Oreal, Paris, France

[21] Appl. No.: 65,443

[22] Filed: Aug. 10, 1979

[30] Foreign Application Priority Data

Aug. 31, 1978 [FR] France .............................. 78 25149

[51] Int. Cl.$^3$ ...................... G01N 3/38; G01N 33/48
[52] U.S. Cl. ...................................... 73/579; 73/789; 128/774
[58] Field of Search ................ 73/579, 778, 824, 789, 73/797; 128/739, 774

[56] References Cited

U.S. PATENT DOCUMENTS

| | | | |
|---|---|---|---|
| 2,960,862 | 11/1960 | Spurr et al. | 73/579 |
| 3,313,148 | 4/1967 | Dautreppe et al. | 73/778 X |
| 4,034,602 | 7/1977 | Woo et al. | 73/579 |
| 4,107,775 | 8/1978 | Ott | 73/579 X |
| 4,170,141 | 10/1979 | Woo | 73/579 |

OTHER PUBLICATIONS

"The Review of Scientific Instruments", vol. 43, No. 12, Dec. 1972, pp. 1786–1788.
Med. & Biol. Engng., vol. 8, pp. 389–393, Jul. 1970.
"23rd Annual Conference on Engineering in Medicine & Biology", Transducer for Studies of Active Muscles, by Kronick et al., Nov. 1970.

Primary Examiner—James J. Gill
Attorney, Agent, or Firm—Brisebois & Kruger

[57] ABSTRACT

Young's modulus and/or the internal damping factor of an elastic material is obtained by subjecting an area of the material to a sustained vibration. The presence of the material being tested changes the resonance of a mechanical resonator and determination of the changed resonance peak enables the required elastic characteristics to be obtained. The sample may be subjected to varying tension during testing and can conveniently be vibrated by signals obtained from a variable frequency generator although, preferably, an electronic circuit for vibrating the resonator has a feed-back loop to operate as an electro-mechanical auto-oscillator.

12 Claims, 6 Drawing Figures

METHOD OF AND APPARATUS FOR THE MEASUREMENT OF AT LEAST ONE MECHANICAL PROPERTY OF AN ELASTIC MATERIAL

DESCRIPTION

For the study of materials and their changes in behaviour following a treatment, it is known to be particularly worthwhile being able to measure their elastic properties and in particular their Young's modulus and their internal damping factor. A number of instruments have already been proposed as a means of obtaining these measurements in the case of hard materials but there is no simple and practical method of measuring these characteristics in the case of soft materials. In particular, there is no apparatus permitting of simple measurement of the Young's modulus and/or internal damping factor of the skin, the hair or certain relatively soft polymers.

An object of the present invention is to provide a method and apparatus which makes it possible easily to measure the elasticity modulus and/or the internal damping factor of numerous ductile materials by a dynamic method consisting of subjecting the material to be tested to a vibration and in deducing, from the resonance peak obtained with the apparatus according to the invention in the presence and in the absence of the sample to be tested, the values for elastic characteristics which it is desired to measure.

According to the present invention there is provided a method of measuring at least one mechanical property of an elastic material, particularly a ductile material of minimal hardness, in which an area of the material to be tested is subjected to a sustained vibration and the resonance frequency of the whole which is subjected to vibration and/or elongations of the material tested as a function of the time or frequencies employed is noted, the material to be tested being so disposed as to modify the resonance phenomenon of a mechanical resonator, and the modification of the resonance phenomenon being used to deduce at least one elastic property of the material tested, taken from the group comprising Young's modulus and the inner damping factor.

The area of material to be tested which is subjected to vibration may be an area of skin of a living subject, measurement being carried out "in vivo". Alternatively the area of material to be tested and subjected to vibration is a sample stretched between a stationary and a vibrating element, measurement being carried out "in vitro".

According to a first alternative embodiment, the method according to the invention is carried out by effecting a frequency scan in order to establish the resonance frequencies; according to a second alternative embodiment, the method according to the invention is carried out by using a loop to make up an auto-oscillator vibrating at the resonance frequency.

Another aspect of the present invention provides apparatus for measuring a mechanical property of an elastic material and comprising a fixed frame; a mobile assembly carried by the frame; an electromagnetic operating device having at least one coil for vibrating the mobile assembly relative to the frame, the said mobile assembly being rigid with a first securing element for securing the sample to be tested and; a second securing element carried by the frame whereby, the sample to be tested may be disposed between the said first and second securing elements; means for displacing the second securing element in the frame for, in use of the apparatus, changing the mechanical tension of a sample secured between the said first and second securing elements; an electronic circuit associated with the electromagnetic operating device for providing a supply of electricity at the appropriate frequency to said coil; and at least one device for the receipt of data provided by the aforesaid electronic circuit.

In cases where it is desired to measure Young's modulus, the sample is disposed between a vibrating mobile assembly and a fixed point and the resonance frequencies of the mechanical vibration of the moving assembly are measured with and without the sample being interposed. The value of Young's modulus is then arrived at by applying the following mathematical formula:

$$E = \frac{4\pi^2 ML (v^2 - v_0^2)}{s}$$

in which M represents the vibrating mass, L the length of the sample tested, s the cross-section of the sample tested, $v$ and $v_0$ representing the resonance frequencies, with and without sample, respectively. The formula given hereinabove asumes that measurements carried out to obtain frequencies $v$ and $v_0$ are performed under substantially constant external conditions, particularly with regard to temperature and relative humidity, and assumes that the forces of viscosity and the mass of the sample in relation to the total mass of the mobile vibrating assembly are disregarded.

It is possible to measure frequencies $v$ and $v_0$ by varying the mechanical stress to which the sample is subject in the rest condition and possibly to measure the relative elongation of this sample under a given mechanical tension, all these measurements being translated to a recorder in the form of traces. In order to determine the resonance frequency of the mobile assembly, whether it is associated with a sample to be tested or not, it is possible to carry out a frequency scan using a variable frequency generator and recording the vibration amplitudes as a function of the frequency in order to determine the resonance peak, the apex of which is obtained for the resonance frequency. However, in order to render measurement automatic, a preferred form of embodiment suggests associating with the vibrating mobile assembly an electronic circuit which, via a feed back loop, makes it possible to provide an electro-mechanical auto-oscillator, the assembly then vibrating automatically at the resonance frequency: to do this, the mobile assembly comprises an electromagnetic coil and the vibration amplitudes are registered by a photo-electric cell, the output signal from which is passed to the coil supply after passing through a controlled gain amplifier system.

Should there be a wish to measure the internal damping factor of the material to be tested, the resonance peak relevant to the vibration of the mobile assembly is recorded and from the width of this peak at mid-height it is possible to deduce the value of the inner damping factor using a known mathematical relationship. Instead of identifying the amplitude of the oscillations in order to determine the resonance peak, it is possible likewise to work with a constant amplitude of vibration, note the energy consumed by the coil which causes vibration of the mobile assembly, and study the peak which translates the decrease in this energy in the vicinity of the resonance frequency, study of this peak likewise leading to measurement of the inner damping factor.

In a preferred form of embodiment, a force measuring means is provided mounting the second securing means for the provision of a signal indicative of the tension in a sample being tested. This makes it possible to record the force/elongation curves; the mobile assembly may be constituted by a metal strip fixed at both ends and carrying in its central zone an electromagnetic coil disposed in the field of a fixed permanent magnet and constituting with it the electromagnetic control device of the apparatus; in the event of the apparatus according to the invention being intended for "in vitro" measurement, the securing element of the mobile assembly and/or the securing element of the sample may comprise a substantially vertical slideway having a dovetail cross-section, the edges of the slideway being downwardly convergent.

In a first alternative embodiment of the apparatus according to the invention, the electronic circuit comprises at least one photoelectric pick-up which registers the vibrations of the mobile assembly. According to a first embodiment of this alternative, intended for automatic measurement of Young's modulus, the photoelectric pick-up of the electronic circuit feeds a low frequency controlled gain amplifier which in turn supplies the coil of the electromagnetic control device; a frequency/tension converter receives as data the frequency of the excitation current of the coil and supplies a recorder which also receives an electrical signal which is a function of the mechanical tension of the sample and/or an electrical signal which is a function of the relative elongation of the sample under tension. In another embodiment according to this first alternative, intended for measuring the internal damping factor of the material to be tested, the photoelectric pick-up, through an amplitude demodulator, feeds a recorder, the coil being energised by a regulatable frequency current generator, an image thereof being transmitted to the said recorder via a frequency/tension converter.

In a second alternative embodiment of the apparatus, the electronic circuit comprises a regulatable frequency current generator, of which an image is transmitted via a frequency/tension converter, to a recorder, the said generator supplying a coil of the electromagnetic control device, an amplitude demodulator measuring the amplitude of the excitation current of the said coil and feeding this information to the aforesaid recorder.

In order to measure the elasticity modulus of the sample by the method according to the invention, it will be found that it is not necessary to go so far as to cause the sample to rupture; in the majority of cases, there is but a slight departure from the realm of elasticity, so that value obtained may be confirmed by repeated measurements on the same sample. The apparatus according to the invention is particularly interesting when it is used for automatic measurement of Young's modulus by direct determination of the resonance frequencies but this measurement may be supplemented by studying the resonance peaks and by studying the mechanical tension as a function of the elongation of the sample while keeping the sample on the same apparatus. Comparison of these three types of measurement reveals that direct measurement of Young's modulus is for practical purposes unaffected by the traction speed when the tractive force applied to the sample is varied, in view of the fact that the traction time is generally considerable in relation to the vibration cycle.

The method and the apparatus of the invention may advantageously be used for examining biological materials and in particular for studying the elastic properties of the Stratum Corneum of the human skin, for studying the skin "in vivo", for studying hair on both head and body, for studying collagen fibres, for studying vegetable or animal fibres such as linen, cotton and the fibres of paper, cellulose, wool or silk. However, the method and the apparatus according to the invention may likewise be used for materials which have no living source, for example polymer fibres such as polyesters, polyamides, polyethylene or rubber, or even for hard materials such as steel or tungsten, it being understood that in this latter case, the cross-section of the sample which is vibrated must be sufficiently small.

For better understanding of the invention, various embodiments of the invention will be described hereinafter, purely by way of example and implying no limitation, reference being made to the accompanying drawings, in which.

Figure 1:
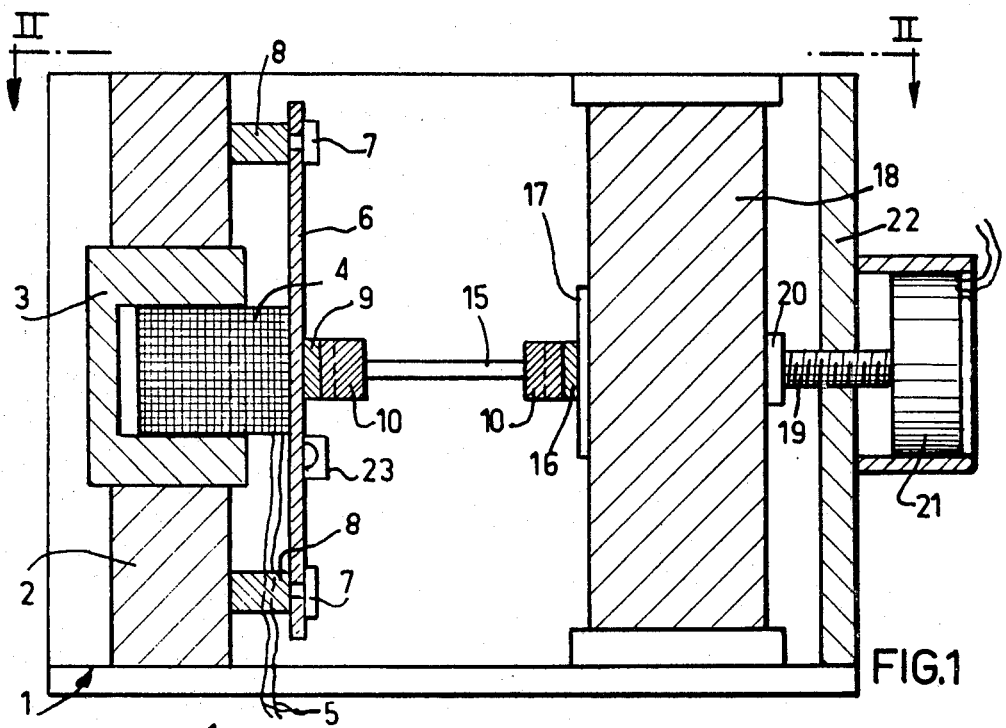
FIG. 1 is a cross-sectional view taken on the line I—I in FIG. 2, showing apparatus embodying the invention for the automatic measurement of Young's modulus.
Figure 2:
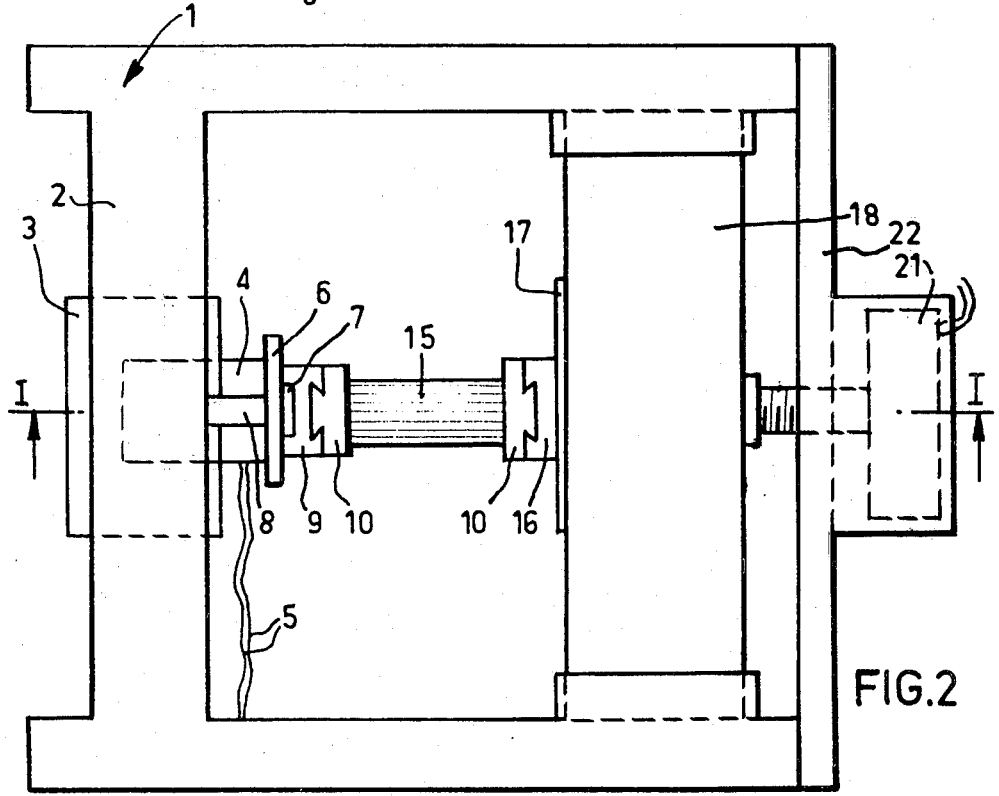
FIG. 2 is a plan view of the apparatus of FIG. 1, taken on the line II—II in FIG. 1.
Figure 3:
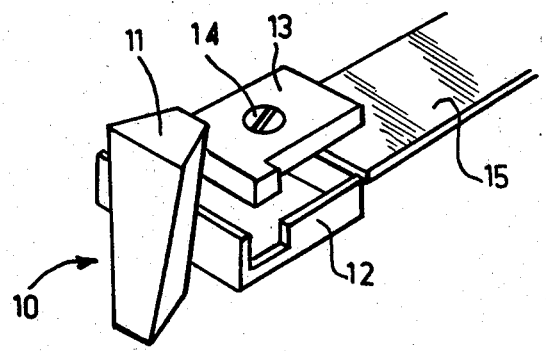
FIG. 3 is a detail perspective view of a fitment for retaining an end of a sample to be tested.
Figure 4:
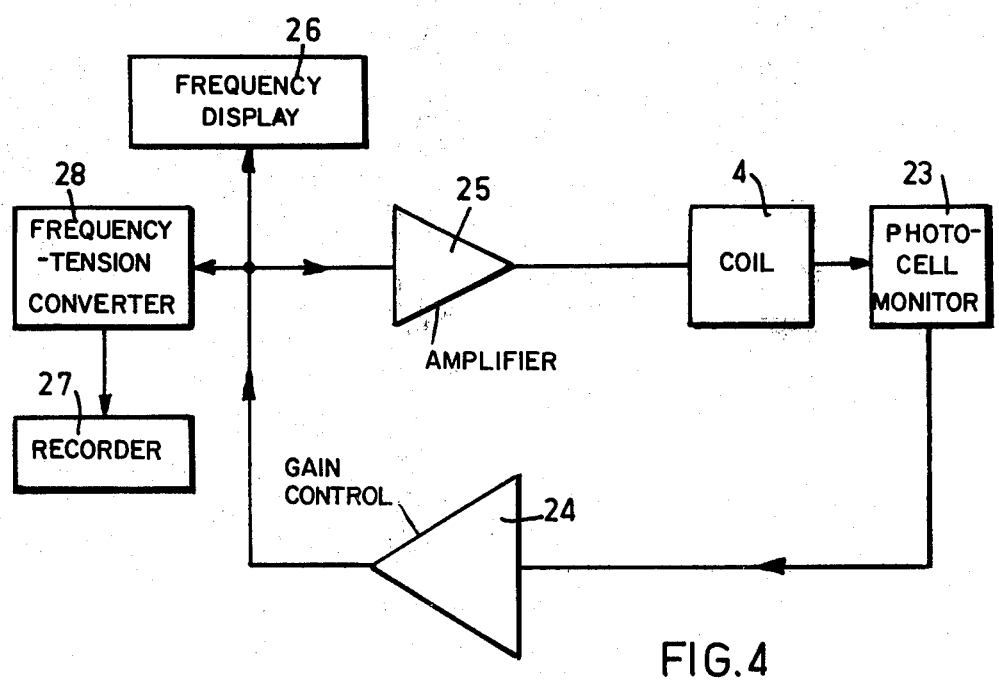
FIG. 4 is a block diagram of an electronic circuit which provides a supply to the electromagnetic coil of the apparatus to cause vibration of the mobile assembly at its resonance frequency.

Referring to the drawings and more particularly to FIGS. 1 to 4, it can be seen that the illustrated apparatus consists of a frame 1 comprising a vertical transverse bar 2 in the central portion of which there is a permanent magnet 3 defining in its central zone a space in which there is an electromagnetic coil 4. The coil 4 is supplied with electric current via wires 5 and is carried at the centre of a rectangular metal plate 6 disposed vertically and clamped at each of its ends to a supporting post 8 by a screw 7. The supporting post 8 is carried by the bar 2. In the central zone of the metal plate 6 there is provided a fixing element 9 comprising a slideway having a dovetail cross-section, the axis of the slideway being substantially vertical and the edges of the slideway being downwardly convergent. This fixing element 9 is designed to co-operate with the male element 10 shown in detail in FIG. 3.

The male element 10 consists of a block 11 of trapezoidal cross-section and of substantially vertical axis, the edges of the block 11 being slightly downwardly convergent. The block 11 is designed to slide in the slideway which has a dovetail cross-section and which is provided on the fixing element 9; convergence of the edges makes it possible to lock the male element 10 in the fixing element 9 when the male element 10 is dropped into the fixing element 9. In this way, when the plate 6 is caused to vibrate, there will be a perfect contact between the fixing element 9 and the male element 10 to ensure reliable measurement. The block 11 is rigid with a female jaw 12 into which it is possible to introduce a male jaw 13 which can be clamped against the female jaw by a screw 14, the screw-threading of which co-operates with a screw-threaded bore provided in the jaw 12. Between the jaws 12 and 13 is introduced one end of the sample 15 which it is desired to subject to testing in the apparatus. The clamping effect of the screw 14 makes it possible to fix the sample 15 rigidly to the block 11 and consequently to the metal place 6 when the male element 10 is introduced into the fixing element 9. That end of the sample 15 which is not connected to the fixing element 9 is connected to a hooking element 16 comprising a slideway having a vertical axis and a dovetail cross-section identical to the slideway of the fixing element 9. The hooking element 16 receives a male element 10 identical to that which co-operates with the fixing element 9, this male element being rigid with the corresponding end of the sample 15, as was previously stated for the end which is connected to the fixing element 9.

The hooking element 16 is carried by a force detector member 17 itself carried by a slide 18 capable of movement in relation to the frame 1. During the course of experiments, the slide 18 may be held fixed in relation to the frame 1 or be slowly moved by means of a screw 19 connected to it by an abutment 20 and caused to rotate by a motor-reduction unit 21 inside a screw-threaded bore provided in a bar 22 of the frame. The motor 21 is non-rotatable in relation to the bar 22 but is capable of movement in relation to the said bar at the same time as the screw 19. It will be appreciated therefore that if current is supplied to the motor reduction unit 21, it is possible to produce a slow movement of the slide 18 in relation to the frame and consequently subject the sample 15 to a more or less considerable tractive stress. By noting the displacement of the slide 18, it is possible to measure the relative elongation of the sample 15, the tractive stress applied to the sample being measured by the force detector 17. It will therefore readily be possible to make a recording of the mechanical tension of the sample as a function of the relative elongation.

When electricity is supplied to the coil 4, as this is in a magnetic field it tends to move axially and if the coil is supplied with a sinusoidal current, the result will be a vibration of the metal plate 6 with which the coil is rigid. The amplitudes of vibration may be established by a photoelectric pick-up 23 fixed to the frame: the light may emanate from a photo diode and be received by a photo transistor. The photoelectric pick-up thus constituted supplies a low frequency amplifier 25, the gain of which is controlled by the device 24 and of which the output supplies the electromagnetic coil 4. By virtue of this feed-back loop, it is automatically possible to supply the coil 4 at the resonance frequency of the mobile assembly comprising the coil 4, the plate 6, the fixing element 9, the male element 10 and the sample 15. Thus, the resonance frequency $v$ is determined in the presence of the sample and functioning of the apparatus without a sample makes it possible in the same way to determine the resonance frequency $vo$ in the absence of a sample. In the embodiment which has been described, the mass of the mobile assembly was approx. 13 grams and the actual resonance frequency of the mobile assembly without a sample was in the region of 250 Hz, the metal plate 6 being 139 mm long, 5.5 mm wide and 1 mm thick, and being of stainless steel.

By applying the mathematical formula indicated at the start of the present description it is possible from frequencies $v$ and $vo$ to calculate Young's modulus for the various materials subjected to test. In this case, it is sufficient to read the vibration frequencies displayed by a frequency meter 26 connected to the input of the low frequency amplifier 25.

If, during the course of the test, current is supplied to the motor reduction unit 21, it is possible to vary the mechanical tension of the sample 15. In this case, for each position of the slide 18, a relative elongation of the sample 15 is defined and this information is passed to a recorder 27. Simultaneously, the mechanical tension of the sample 15 is measured by a force detector 17 which makes it possible to obtain on the recorder 27 a first trace showing the tractive stresses as a function of the elongations. Moreover, the information corresponding to the frequency $v$ is transformed by means of a frequency/tension converter 28 and the resultant signal from the converter 28 is transmitted to the recorder 27 to obtain a second trace showing the fluctuation in frequency $v$ as a function of the relative elongation of the sample. It can be seen therefore that without any difficulty it is possible to obtain on the recorder 27 two traces by means of which the elastic behaviour of the sample can be fully determined. Measurement having been carried out, by viture of its dynamic nature, it is for practical purposes insensitive to the speed of traction because the traction time is generally considerable in relation to the vibration cycle.

By means of the apparatus which has just been described, it has been possible to measure "in vitro" the elasticity modulus of the Stratum Corneum of the human skin: the result was $3 \times 10^9$ dyn/sq.cm at 30° C. and at 70°% relative humidity. It was likewise possible to establish the importance of the effect of certain products applied to the skin in respect of the elastic properties of the Stratum Corneum. Moreover, the elasticity modulus of a natural hair was likewise measured at 20° C. and 30% relative humidity, the result being $7 \times 10^{10}$ dyn/sq.cm; it was possible accurately to study the effect of cosmetic treatment or bleaching on the elasticity modulus of the hair.

Figure 5:
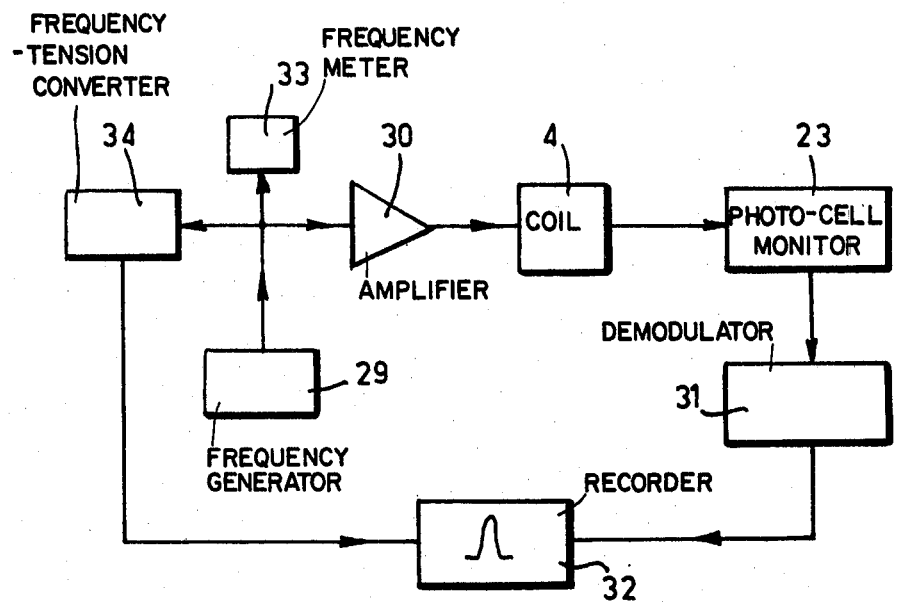
FIG. 5 is a block diagram of an electronic circuit for scanning frequencies and for obtaining a resonance peak on a recorder.

FIG. 5 shows the block diagram of a slightly different electronic circuit which may be associated with the apparatus. According to this diagram, a low frequency generator which can be frequently modulated, 29, supplies a low frequency amplifier 30, the output of which is connected to the coil 4 of the apparatus. The photoelectric cell 23 which detects the amplitudes of vibration, transmits a signal to an amplitude demodulator 31 which allows vibration amplitudes to be noted, and the output from the amplitude demodulator supplies a recorder 32. Furthermore, the frequency emitted by the generator 29 is both measured by a frequency meter 33 and transformed by a frequency/tension converter 34 into a signal which is likewise passed to the recorder 32. Thus, the recorder 32 makes it possible to trace a curve showing the amplitude of vibration as a function of the frequency, that is to say a peak is obtained for the resonance frequency. Study of this peak makes it possible not only to determine, from the abscissa of the maximum, the resonance frequency and at the same time Young's modulus, but also to determine the internal damping coefficient of the material tested, by means of the width of the peak at mid-height.

Figure 6:
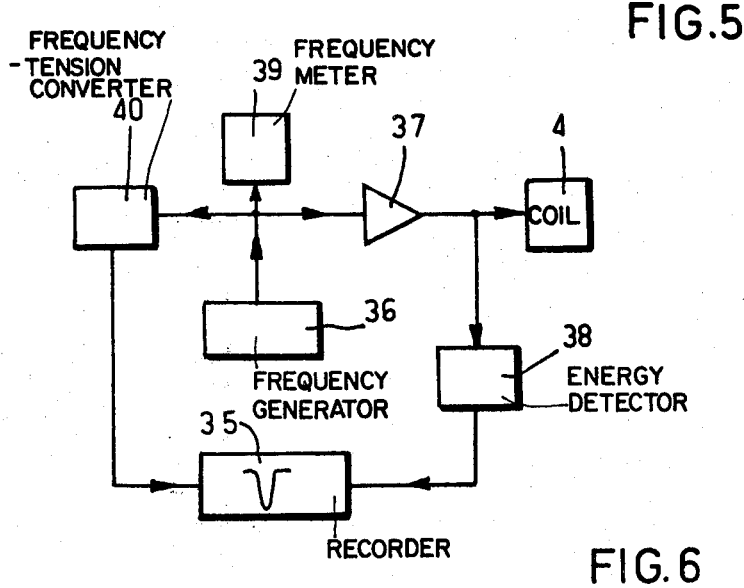
FIG. 6 is a block diagram of an electronic circuit which, by frequency scanning, makes it possible and as a function of the frequency, to record the energy needed to maintain the vibration of the mobile assembly.

FIG. 6 shows the block diagram of an alternative circuit which likewise makes it possible on a recorder 35 to obtain a peak at the moment of passing through the resonance frequency. In this circuit, as in the circuit shown in FIG. 5, frequency scanning takes place by means of a low frequency generator 36 which can be frequency modulated. The generator 36 supplies a low frequency amplifier 37, the output of which is connected to the coil 4 and to an apparatus 38 which permits the energising current of the coil 4 to be measured. The output of the apparatus 38 is a signal proportional to the energy absorbed by the coil 4 and this signal is passed to the recorder 35. The frequency of the supply to the coil 4 is measured by a frequency meter 39 and the information corresponding to the frequency is passed to the recorder 35 via a frequency/tension converter 40. At the moment of passing through the resonance frequency, there appears on the recorder 35 a negative peak since the energy passed to the coil 4 passes through a minimum at the resonance frequency. Study of this peak, like study of the peak obtained on the recorder 32 in the circuit shown in FIG. 5, makes it possible to determine the internal damping factor of the material subjected to test.

We claim:

1. Apparatus for measuring a mechanical property of an elastic material comprising, a fixed frame; a mobile assembly carried by the frame; an electromagnetic operating device having at least one coil for vibrating the mobile assembly relative to the frame, said mobile assembly having a first securing element rigid therewith for securing the sample to be tested; a second securing element carried by the frame whereby the sample to be tested may be disposed and held between the said first and second securing elements; means for displacing the second securing element in the frame for, in use of the apparatus, changing the mechanical tension of a sample secured between the said first and second securing elements; an electronic circuit associated with the electromagnetic operating device for providing a supply of electricity at the appropriate frequency to said coil; at least one device for the receipt of data provided by the aforesaid electronic circuit, and force measuring means mounting the second securing means for providing a signal indicative of the tension in a sample being tested.

2. Apparatus according to claim 1, wherein the data receiving device is a recorder.

3. Apparatus according to claim 2, wherein the recorder comprises data display means.

4. Apparatus according to claim 1, wherein the mobile assembly comprises a metal plate fixed to the frame at both ends and carrying at its center an electromagnetic coil disposed in the field of a fixed permanent magnet carried by the frame.

5. Apparatus according to claim 1, wherein at least one of the securing elements comprises a substantially vertical slideway having a dovetail cross-section with downwardly convergent edges.

6. Apparatus according to claim 1, wherein the electronic circuit comprises at least one photo-electric pick-up arranged to monitor the vibration of the mobile assembly.

7. Apparatus according to claim 6, wherein the electronic circuit includes a low-frequency amplifier, the gain of which is automatically controlled, the amplifier receiving a signal from the photo-electric pick-up and in turn supplying the coil of the electromagnetic operating device.

8. Apparatus for measuring a mechanical property of an elastic material comprising, a fixed frame; a mobile assembly carried by the frame; an electromagnetic operating device having at least one coil for vibrating the mobile assembly relative to the frame, the said mobile assembly having a first securing element rigid therewith for securing the sample to be tested; a second securing element carried by the frame whereby the sample to be tested may be disposed and held between the said first and second securing elements; means for displacing the second securing element in the frame for, in use of the apparatus, changing the mechanical tension of a sample secured between the said first and second securing elements; an electronic circuit associated with the electromagnetic operating device for providing a supply of electricy at the appropriate frequency to said coil; at least one device for the receipt of data provided by the aforesaid electronic circuit, said electronic circuit comprising at least one photo-electric pick-up arranged to monitor the vibration of the mobile assembly, and a low-frequency amplifier, the gain of which is automatically controlled, the amplifier receiving a signal from the photo-electric pick-up and in turn supplying the coil of the electromagnetic operating device, and a frequency/tension converter arranged to correlate the frequency of the coil exciter current with one of the tension and elongation of a sample being tested to provide an output signal to the data receiving device.

9. Apparatus for measuring a mechanical property of an elastic material and comprising a fixed frame; a mobile assembly carried by the frame; an electromagnetic operating device having at least one coil for vibrating the mobile assembly relative to the frame, the said mobile assembly having a first securing element rigid therewith for securing the sample to be tested; a second securing element carried by the frame whereby the sample to be tested may be disposed and held between the said first and second securing element; means for displacing the second securing element in the frame for, in use of the apparatus, changing the mechanical tension of a sample secured between the said first and second securing elements; an electronic circuit associated with the electromagnetic operating device for providing a supply of electricity at the appropriate frequency to said coil; at least one device for the receipt of data provided by the aforesaid elecronic circuit, said electronic circuit comprising at least one photo-electric pick-up arranged to monitor the vibration of the mobile assembly, and including an amplitude demodulator, a regulatable frequency current generator and a frequency/tension converter, the photo-electric pick-up being arranged to feed the data receiving device via its amplitude demodulator with the coil being energized by the regulatable frequency current generator, the output signal from which is also passed through the frequency/tension converter to the data receiving means.

10. Apparatus for measuring a mechanical property of an elastic material and comprising, a fixed frame; a mobile assembly carried by the frame; an electromagnetic operating device having at least one coil for vibrating the mobile assembly relative to the frame, the said mobile assembly having a first securing element rigid therewith for securing the sample to be tested; a second securing element carried by the frame whereby the sample to be tested may be disposed and held between the said, first and second securing elements; means for displacing the second securing element in the frame for, in use of the apparatus, changing the mechanical tension of a sample secured between the said first and second securing elements; an electronic circuit associated with the electromagnetic operating device for providing a supply of electricity at the appropriate frequency to said coil; at least one device for the receipt of data provided by the aforesaid electronic circuit, said electronic circuit comprising a regulatable frequency current generator, a frequency/tension generator, and an amplitude demodulator, the generator supplying a signal, via the frequency/tension converter, to the data receiving means an also feeding said coil of the electromagnetic operating device, the amplitude demodulator being arranged for measuring the amplitude of the current energizing said coil and supplying this information to the data receiving means.

11. Apparatus according to claim 10, including a frequency meter to measure the frequency of the current energizing said coil of the electromagnetic operating device.

12. Apparatus for measuring a mechanical property of an elastic material and comprising, a fixed frame; a mobile assembly carried by the frame; an electromagnetic operating device having at least one coil for vibrating the mobile assembly relative to the frame, the said mobile assembly having a first securing element rigid therewith for securing the sample to be tested; a second securing element carried by the frame whereby the sample to be tested may be disposed and held between the said first and second securing elements; means for displacing the second securing element in the frame for, in use of the apparatus, changing the mechanical tension of a sample secured between the said first and second securing elements; an electronic circuit associated with the electromagnetic operating device for providing a supply of electricity at the appropriate frequency to said coil; at least one device for the receipt of data provided by the aforesaid electronic circuit, said electronic circuit comprising at least one photo-electric pick-up arranged to monitor the vibration of the mobile assembly, a low-frequency amplifier, the gain of which is automatically controlled, the amplifier receiving a signal from the photo-electric pick-up and in turn supplying the coil of the electromagnetic operating device, and a frequency meter measuring the frequency of the current which energizes said coil of the electromagnetic operating device.

* * * * *